(12) United States Patent
Valaie et al.

(10) Patent No.: US 10,806,894 B2
(45) Date of Patent: Oct. 20, 2020

(54) CATHETER HUB WITH SEALED ACCESS PORT

(71) Applicant: Cook Medical Technologies LLC, Bloomington, IN (US)

(72) Inventors: Arman H. Valaie, Bloomington, IN (US); Gary L. Neff, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 444 days.

(21) Appl. No.: 15/416,464

(22) Filed: Jan. 26, 2017

(65) Prior Publication Data
US 2017/0232230 A1  Aug. 17, 2017

Related U.S. Application Data

(60) Provisional application No. 62/293,936, filed on Feb. 11, 2016.

(51) Int. Cl.
| | |
|---|---|
| *A61M 25/00* | (2006.01) |
| *A61M 25/01* | (2006.01) |
| *A61M 25/09* | (2006.01) |
| *A61M 39/10* | (2006.01) |

(52) U.S. Cl.
CPC .... *A61M 25/0097* (2013.01); *A61M 25/0043* (2013.01); *A61M 25/0133* (2013.01); *A61M 25/0147* (2013.01); *A61M 25/09* (2013.01); *A61M 39/1011* (2013.01);
(Continued)

(58) Field of Classification Search
CPC ........... A61M 2025/09125; A61M 2039/1072; A61M 25/0097; A61M 39/1011; A61M 2025/0163; A61M 2039/062; A61M 2039/0633
See application file for complete search history.

(56) References Cited

U.S. PATENT DOCUMENTS

| | | | |
|---|---|---|---|
| 5,084,015 A | 1/1992 | Moriuchi | |
| 5,399,165 A * | 3/1995 | Paul, Jr. | ............ A61M 25/0147 604/174 |
| 5,522,400 A | 6/1996 | Williams | |
| (Continued) | | | |

FOREIGN PATENT DOCUMENTS

WO  WO 2012/171193 A1  12/2012

*Primary Examiner* — Scott J Medway
*Assistant Examiner* — Courtney B Fredrickson
(74) *Attorney, Agent, or Firm* — Woodard, Emhardt, Henry, Reeves and Wagner LLP

(57) ABSTRACT

A catheter hub for use with a medical device and a catheter, the hub includes a hub body defining a fluid passageway in communication with a first aperture. Optionally, the hub body defines a second aperture that intersects the first aperture. The hub body attaches to the catheter wherein the fluid passageway and the catheter are aligned for fluid flow therethrough. The first aperture extends from and communicates with the fluid passageway to an exterior surface of the hub body and the first aperture configured to receive the medical device. The second aperture extends from and communicates with the first aperture and the exterior surface. A sealing element is sized for and positioned in either the first or the second apertures. The sealing element is configured to receive the medical device and seal both of the first and the second apertures.

17 Claims, 8 Drawing Sheets

(52) U.S. Cl.
CPC ............... *A61M 2025/0063* (2013.01); *A61M 2025/09125* (2013.01); *A61M 2039/1072* (2013.01)

(56) References Cited

U.S. PATENT DOCUMENTS

| | | |
|---|---|---|
| 5,618,267 A | 4/1997 | Palestrant |
| 6,159,177 A | 12/2000 | Amos, Jr. et al. |
| 6,605,075 B1 | 8/2003 | Burdulis |
| 6,673,060 B1 | 1/2004 | Fleming, III |
| 6,699,233 B2 | 3/2004 | Slanda et al. |
| 7,217,256 B2 | 5/2007 | Di Palma |
| 7,520,869 B2 | 4/2009 | Lampropoulos et al. |
| 7,641,630 B2 | 1/2010 | Accisano, III et al. |
| 7,909,814 B2 | 3/2011 | Accisano, III et al. |
| 8,006,953 B2 | 8/2011 | Bennett |
| 8,177,773 B2 * | 5/2012 | Ovcharchyn ......... A61M 25/04 604/533 |
| 8,496,645 B2 | 7/2013 | Eells et al. |
| 2004/0167478 A1 | 8/2004 | Mooney et al. |
| 2005/0137580 A1 | 6/2005 | Raulerson et al. |
| 2006/0212023 A1 | 9/2006 | Cross |
| 2008/0125756 A1 | 5/2008 | Dicarlo et al. |
| 2009/0306606 A1 | 12/2009 | Lancette et al. |
| 2010/0204648 A1 | 8/2010 | Stout et al. |
| 2010/0256487 A1 | 10/2010 | Hawkins et al. |
| 2011/0054447 A1 * | 3/2011 | Johnson ................ A61M 1/008 604/540 |
| 2011/0098682 A1 | 4/2011 | Ahmed et al. |
| 2011/0313403 A1 * | 12/2011 | Hruska ............ A61M 25/0097 604/540 |
| 2013/0090608 A1 | 4/2013 | Stout et al. |
| 2013/0237925 A1 | 9/2013 | Trainer et al. |
| 2014/0088610 A1 | 3/2014 | Bonnette et al. |
| 2014/0128820 A1 | 5/2014 | Braga et al. |
| 2014/0378905 A1 | 12/2014 | Senatore |

\* cited by examiner

CATHETER HUB WITH SEALED ACCESS PORT

CROSS-REFERENCE TO RELATED APPLICATION

This application claims the benefit of U.S. Provisional Application No. 62/293,936 filed Feb. 11, 2016, which is hereby incorporated by reference.

BACKGROUND

The present disclosure relates generally to medical technology and in particular aspects to catheter hubs attachable to catheters that require additional access port therefrom, and related systems.

Catheters are used in a variety of medical procedures, including various catheterization procedures such as drainage of the bladder, kidney or biliary system, abscesses, other sites of fluid collection, and other minimally invasive procedures requiring access to a patient's vasculature or internal cavities. Catheters are also used as feeding tubes for stomach or intestinal access, and other forms of access to a patient's internal cavities to enable fluid communication therein. Catheters are also frequently used with introducer devices. Some catheters have externally-communicating suture lumens in their hubs with a silicone or rubber plug positioned in the hub that is used to seal around the suture. The silicone or rubber plug is used to seal around the suture and pressure is applied onto the plug for sealing around the suture when the catheter is in a locked position. However, these types of catheters can be prone to leaking fluids and/or gases, especially when the catheters are in the unlocked state. After a first catheter is already positioned in the patient's body it is often determined that other procedures requiring rapid access or needle access to a patient's internal body to handle suture, wire guide, administer drugs, pull a blood sample or other liquid is needed which then requires a second catheterization procedure. A second catheterization procedure is costly and painful for the medical patient and requires additional medical resources and practitioners to implant. Additionally, in some situations, a catheter may stay within a patient for an extended period of time, in which case a bulky hub is uncomfortable for the patient and difficult to wear and hide for an active patient.

There remain needs for devices, systems and methods for gaining access to the inside lumen of a catheter hub without adding bulk to the overall profile of the hub and without disconnecting the main access port of catheter hub. The present disclosure is addressed to those needs.

SUMMARY

Aspect 1 concerns a catheter hub for use with a medical device and a catheter, the catheter hub comprising a hub body defining a fluid passageway in communication with an aperture, the hub body adapted for attachment to the catheter, the fluid passageway and the catheter aligned for fluid flow therethrough, the aperture extending from and communicating with the fluid passageway to an exterior surface of the hub body; and a sealing element configured to receive the medical device, the sealing element sized for and positioned in the aperture, wherein the sealing element and the aperture each have a corresponding complementary shape to form a fluid-tight seal between the sealing element and the aperture, the sealing element being fully retained within the aperture.

Aspect 2 concerns the catheter according to aspect 1, wherein the medical device includes a tension member.

Aspect 3 concerns the catheter according to aspect 1, wherein the aperture includes a transition shaft portion that spans between an interior shaft portion and an exterior shaft portion, the interior shaft portion configured to engage the fluid passageway, the exterior shaft portion configured to engage an exterior surface of the hub body; and the sealing element includes a transition shaft member that spans between an interior shaft member and an exterior shaft member wherein the transition shaft member is sized to fill the transition shaft portion, the interior shaft member is sized to fill the interior shaft portion, the exterior shaft member is sized to fill the exterior shaft portion.

Aspect 4 concerns the catheter according to aspect 3, wherein the interior shaft portion, the transition shaft portion, and the exterior shaft portion each have a cylindrical cross-sectional shape, wherein a diameter of the interior shaft portion is smaller than a diameter of the exterior shaft portion, and a diameter of the transition shaft portion tapers from the exterior shaft portion to the interior shaft portion.

Aspect 5 concerns the catheter according to aspect 1, wherein the sealing element is made of silicon, thermoplastic, or polyisoprene material, or a combination of these materials.

Aspect 6 concerns the catheter according to aspect 1, further comprising a locking arm attached to the hub body, the locking arm having a distal locking arm portion adjacent a proximal locking arm portion, the distal locking arm portion configured to cover the aperture.

Aspect 7 concerns the catheter according to aspect 6, wherein the locking arm includes a joint positioned between the distal locking arm portion and the proximal locking arm portion such that either the distal locking arm portion or the proximal locking arm portion can rotate about the joint.

Aspect 8 concerns a catheter hub for use with a medical device and a catheter, the catheter hub comprising a hub body defining a fluid passageway in communication with a first aperture, the hub body defining a second aperture that intersects the first aperture, the hub body adapted for attachment to the catheter, the fluid passageway and the catheter aligned for fluid flow therethrough, the first aperture extending from and communicating with the fluid passageway to an exterior surface of the hub body, the first aperture configured to receive the medical device, the second aperture extending from and communicating with the first aperture and the exterior surface; and a sealing element configured to receive the medical device, the sealing element sized for and positioned in the second aperture wherein the sealing element is configured to move in the second aperture to seal both of the first aperture and the second aperture.

Aspect 9 concerns the catheter according to aspect 8, wherein the sealing element is compressible, and the sealing element is fully retained within the second aperture.

Aspect 10 concerns the catheter according to aspect 8, further comprising a locking device attached to the hub body, the locking device configured to engage the sealing element and compress the sealing element in the second aperture.

Aspect 11 concerns the catheter according to aspect 10, wherein the locking device has a nub configured to engage the sealing element.

Aspect 12 concerns the catheter according to aspect 8, wherein the second aperture intersects the first aperture at an acute angle.

Aspect 13 concerns the catheter according to aspect 8, wherein the sealing element and the second aperture each have a corresponding complementary shape to form a fluid-tight seal between the sealing element and the second aperture.

Aspect 14 concerns a catheter hub for use with a medical device and a catheter, the catheter hub comprising a hub body defining a fluid passageway in communication with a first aperture, the hub body defining a second aperture that intersects the first aperture, the hub body adapted for attachment to the catheter, the fluid passageway and the catheter aligned for fluid flow therethrough, the first aperture extending from and communicating with the fluid passageway to an exterior surface of the hub body, the first aperture configured to receive the medical device, the second aperture extending from and communicating with the first aperture and the exterior surface; and a sealing element configured to receive the medical device, the sealing element sized for and positioned in both of the first aperture and the second aperture.

Aspect 15 concerns the catheter according to aspect 14, wherein the sealing element is configured to move in the second aperture to seal both of the first aperture and the second aperture.

Aspect 16 concerns the catheter according to aspect 14, wherein the second aperture intersects the first aperture at an acute angle.

Aspect 17 concerns the catheter according to aspect 14, further comprising a locking device attached to the hub body, the locking device configured to engage the sealing element and move the sealing element in the second aperture.

Aspect 18 concerns the catheter according to aspect 17, the locking device having a nub configured to engage the sealing element.

Aspect 19 concerns the catheter according to aspect 17, wherein the sealing element is compressed by the locking device.

Aspect 20 concerns the catheter according to aspect 14, further comprising a locking device that includes the sealing element mounted thereon.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
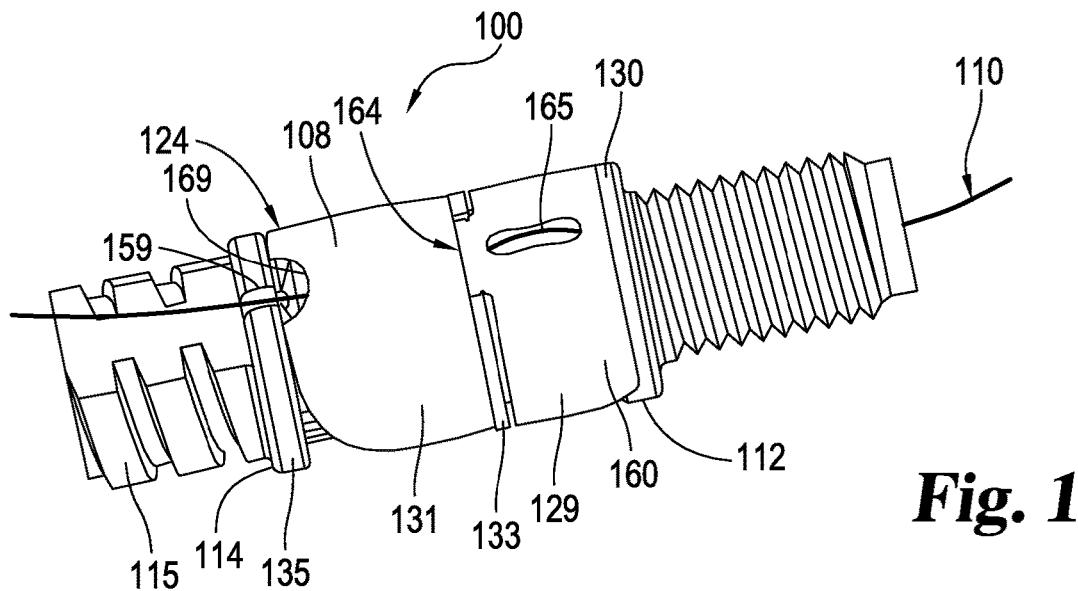
FIG. 1 is a perspective view of a catheter hub with a locking arm attached in a locked configuration.
Figure 2:
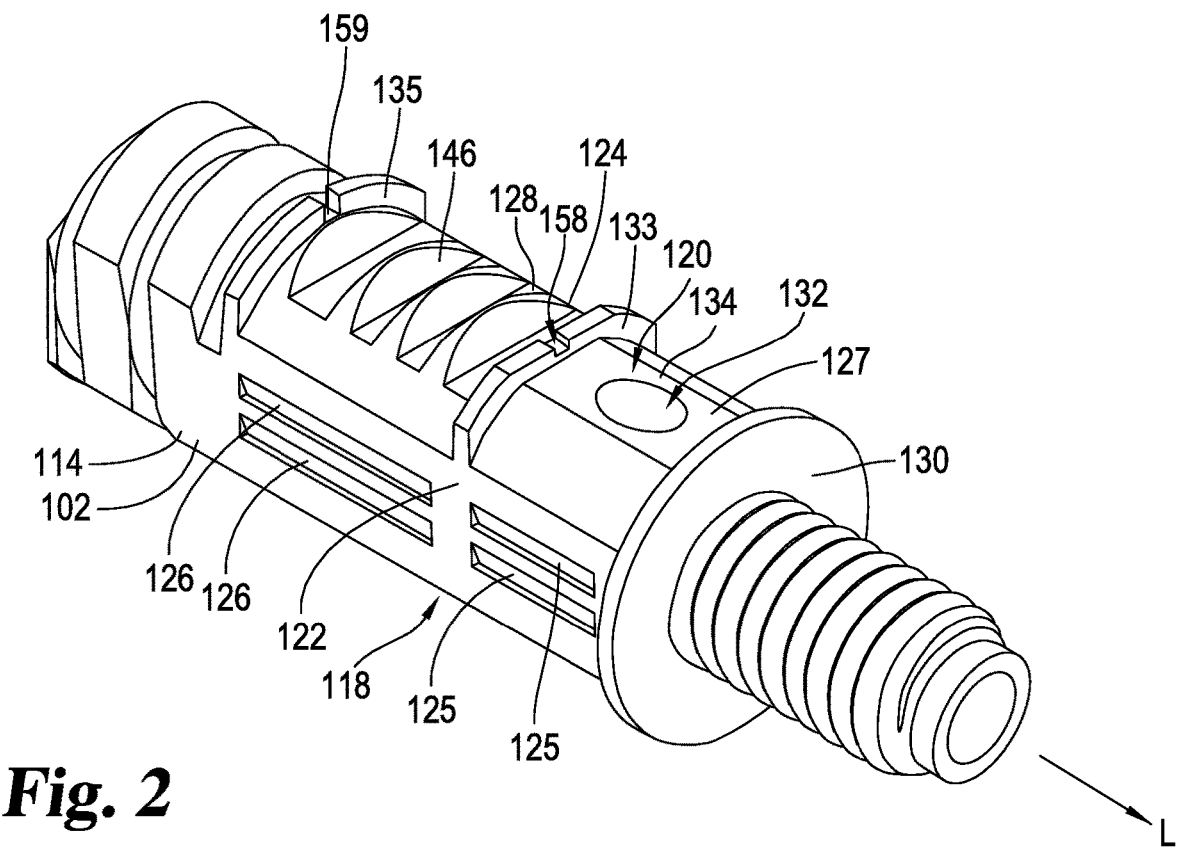
FIG. 2 is a perspective view of a hub body of FIG. 1 without the locking arm attached.
Figure 3:
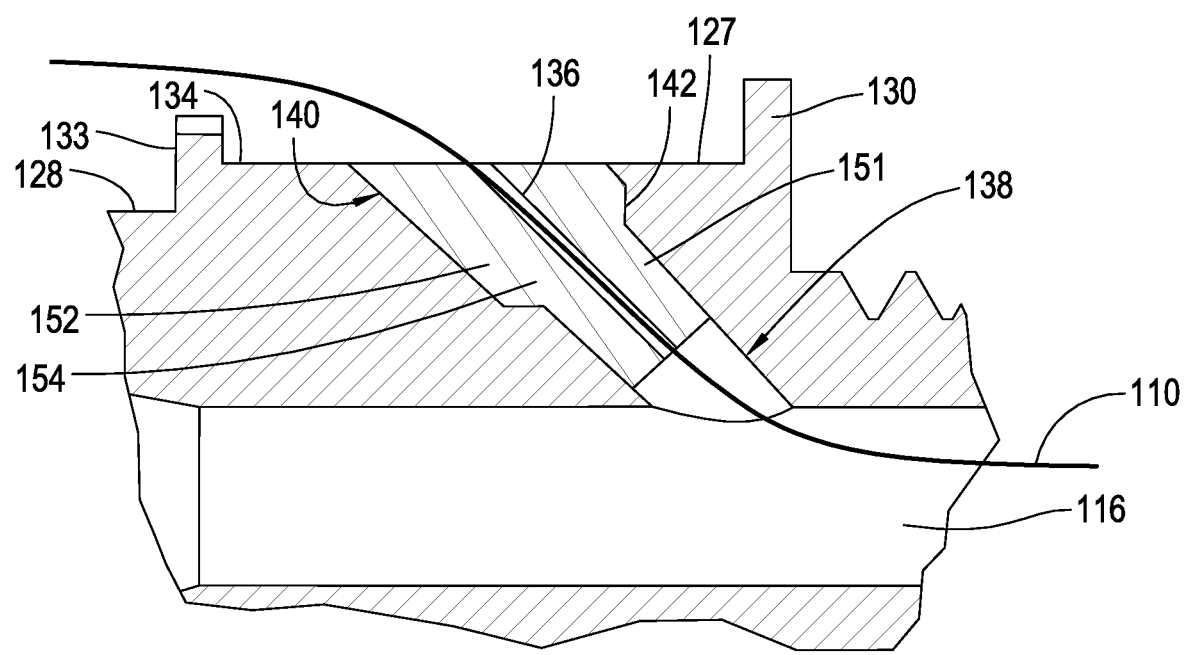
FIG. 3 is a partial cross-sectional view of an aperture and a sealing element from FIG. 1.
Figure 4:
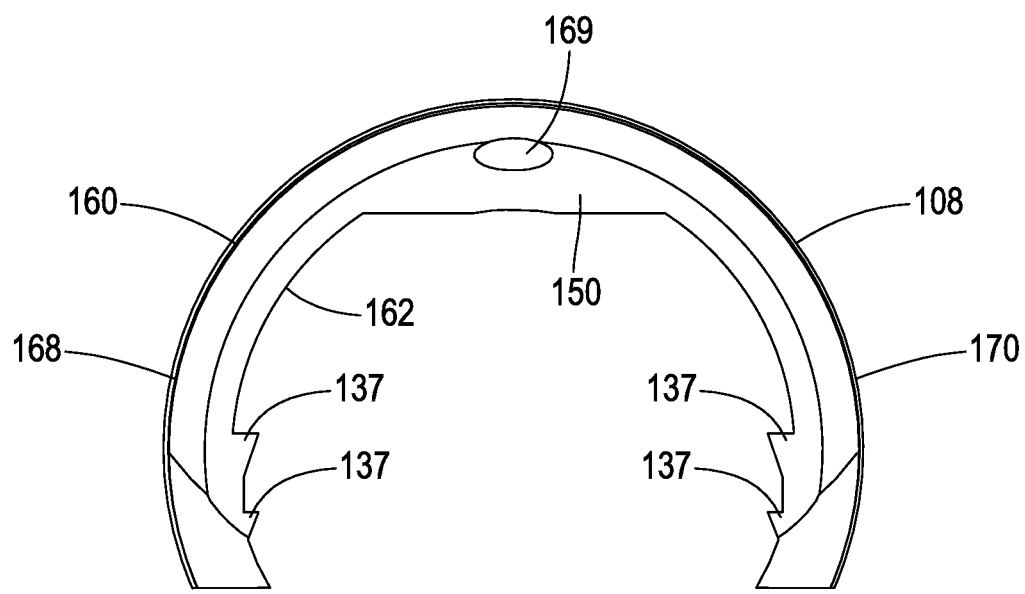
FIG. 4 is an end view of the locking arm of FIG. 1.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

In the following discussion, the terms "proximal" and "distal" will be used to describe the opposing axial ends of the catheter, as well as the opposing axial ends of component features, such as the catheter hub. The term "proximal" is used in its conventional sense to refer to the end of the catheter, or component feature, that is closest to the operator during use. The term "distal" is used in its conventional sense to refer to the end of the catheter, or component feature, that is initially inserted into the patient, or that is closest to the patient during use.

In certain aspects, the present disclosure provides devices, methods and systems for providing rapid access or needle access to handle suture, wire guide, administer drugs, pull blood sample or any other liquids through a catheter and prevent leakage through a catheter hub. For example, typical vascular access through the proximal end of the catheter and into the patient is present; however, the present application is directed to a second access port through the same catheter thereby eliminating the need to place a second catheter in the patient. The catheter hub includes an aperture that is sealed; however, the aperture is accessible by a medical device, suture, wire guide, a needle, a tension member, or other similarly thin medical device to pass through and into a fluid passageway of the catheter hub. For example, the catheter hub according to the present disclosure enables a wire guide to be placed to access vessels of a patient and contrast or medicine to be administered to the patient through the single catheter hub without removing the wire guide. The catheter hub according to the present disclosure provides two or more ports for internal access to a medical patient. The catheter hub according to the present disclosure can also be used with a catheter used as a feeding tube for insertion into a patient's gastrointestinal system. The catheter hub according to the present disclosure is compact which enables the catheter hub to pass through an introducer to enable a doctor to place the catheter through the introducer before pulling the introducer out of the patient during surgery which saves time and resources.

Figure 5:
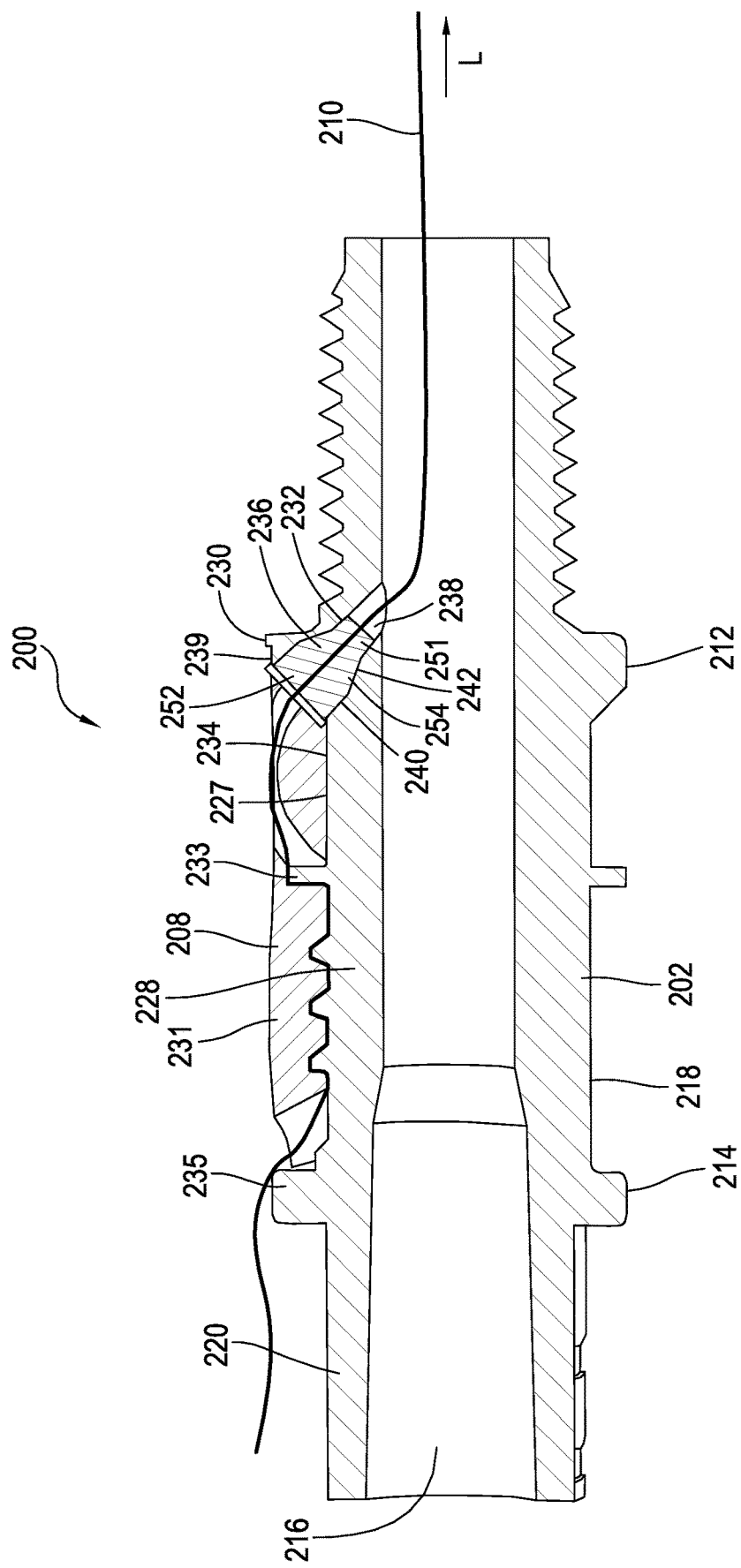
FIG. 5 is a cross-sectional view of a catheter hub with a locking arm in a locked configuration.
Figure 6:
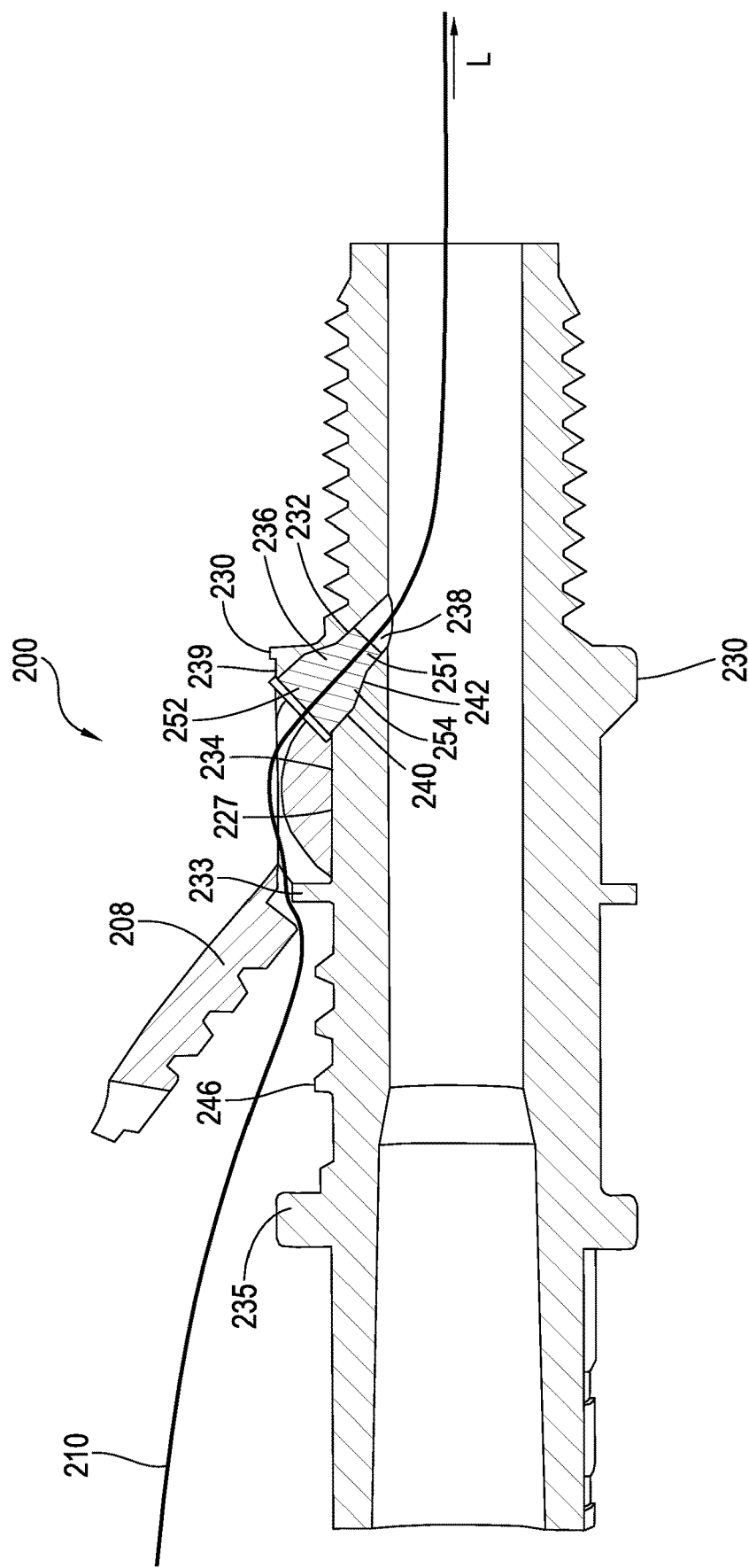
FIG. 6 is a cross-sectional view of the catheter hub of FIG. 5 with the locking arm in an unlocked configuration.
Figure 7:
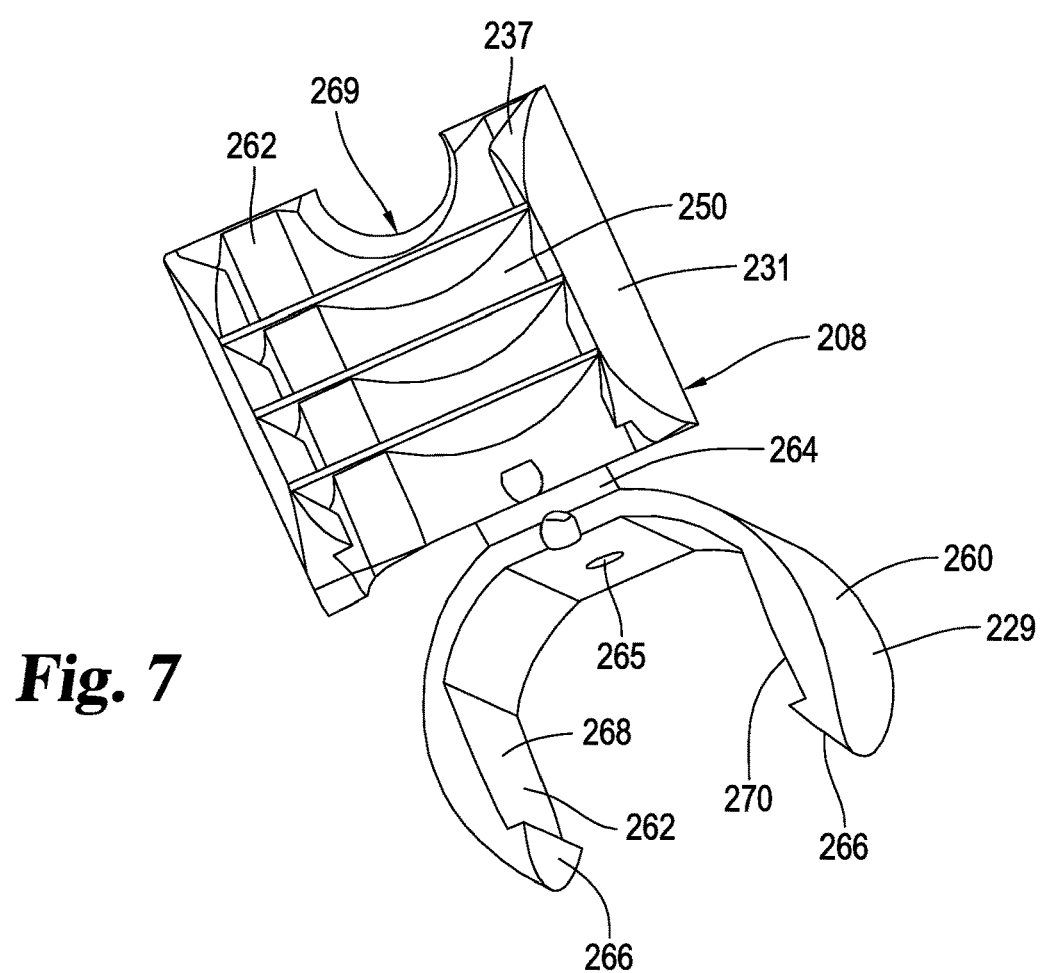
FIG. 7 is a bottom view of the locking arm from the catheter hub of FIG. 5.
Figure 8:
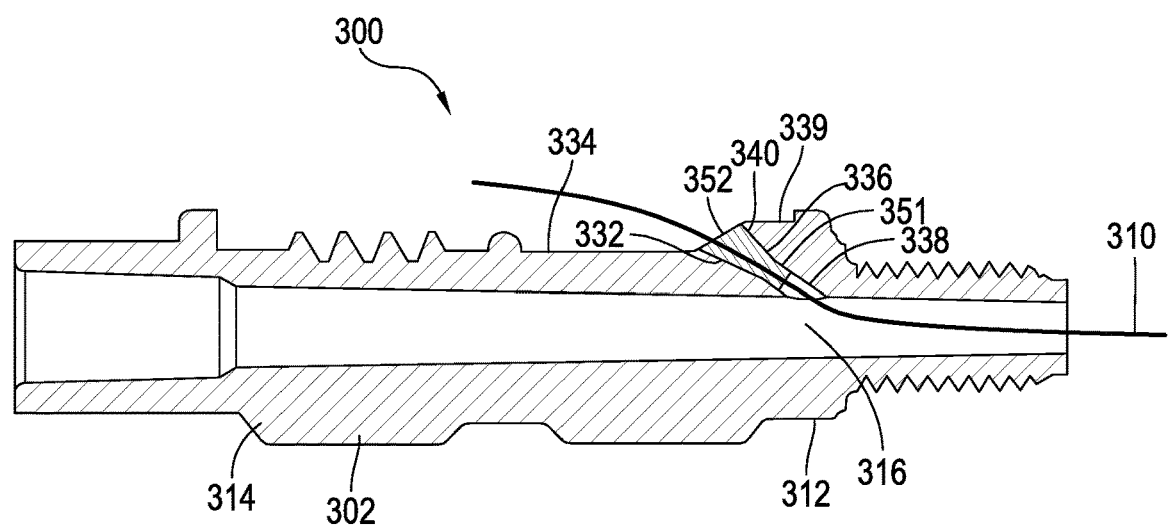
FIG. 8 is a cross-sectional view of a catheter hub.
Figure 9:
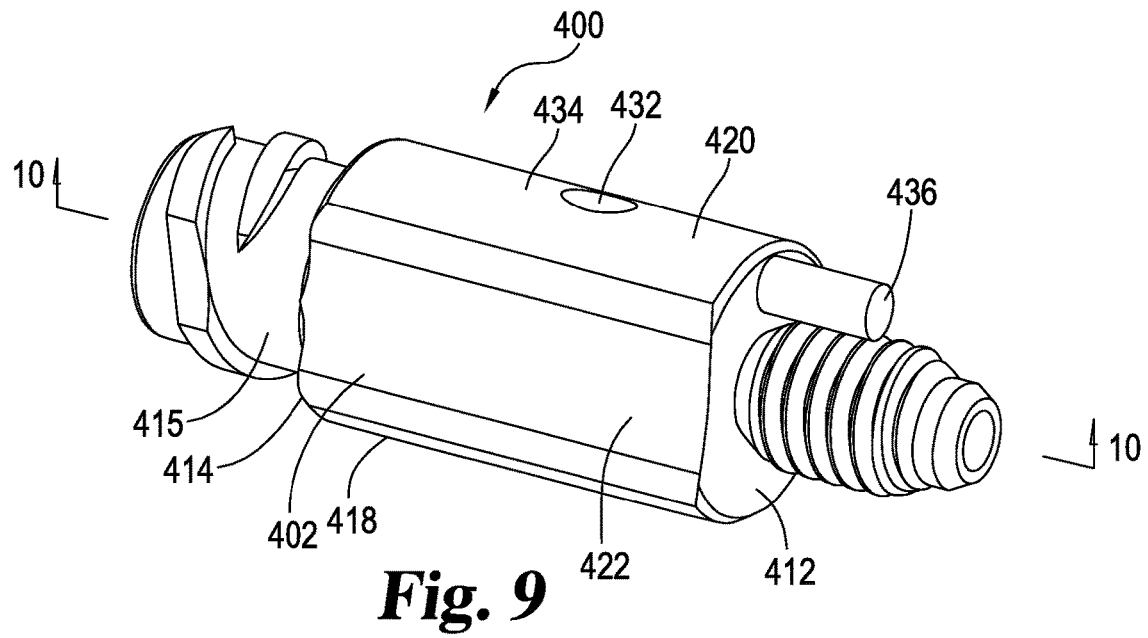
FIG. 9 is a perspective view of a catheter hub in an open position.
Figure 10:
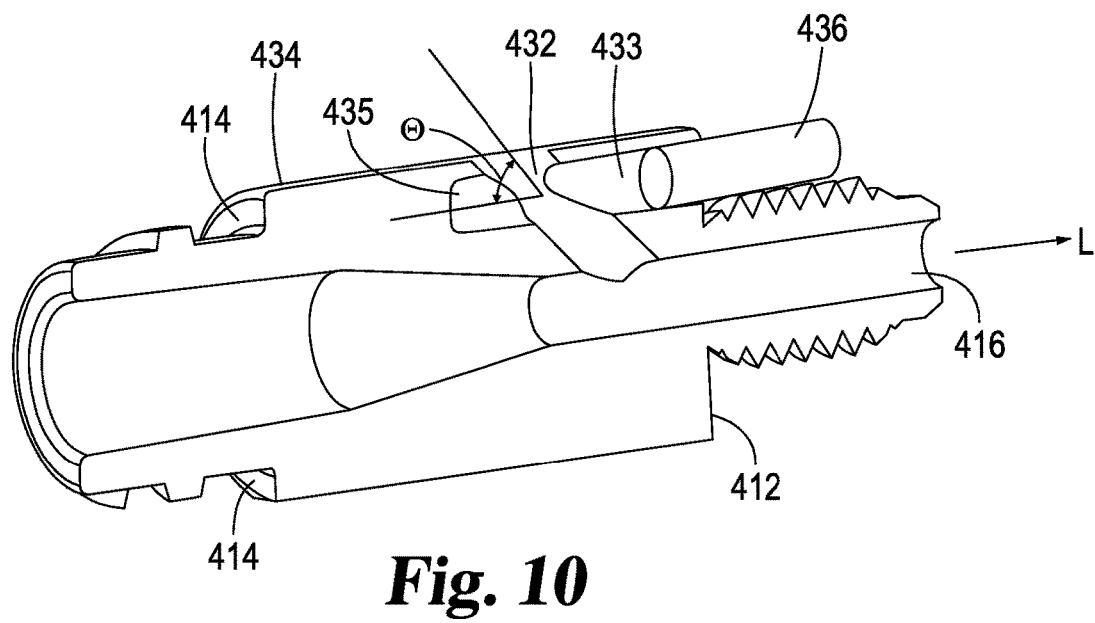
FIG. 10 is a cross-sectional view of the catheter hub of FIG. 9.
Figure 11:
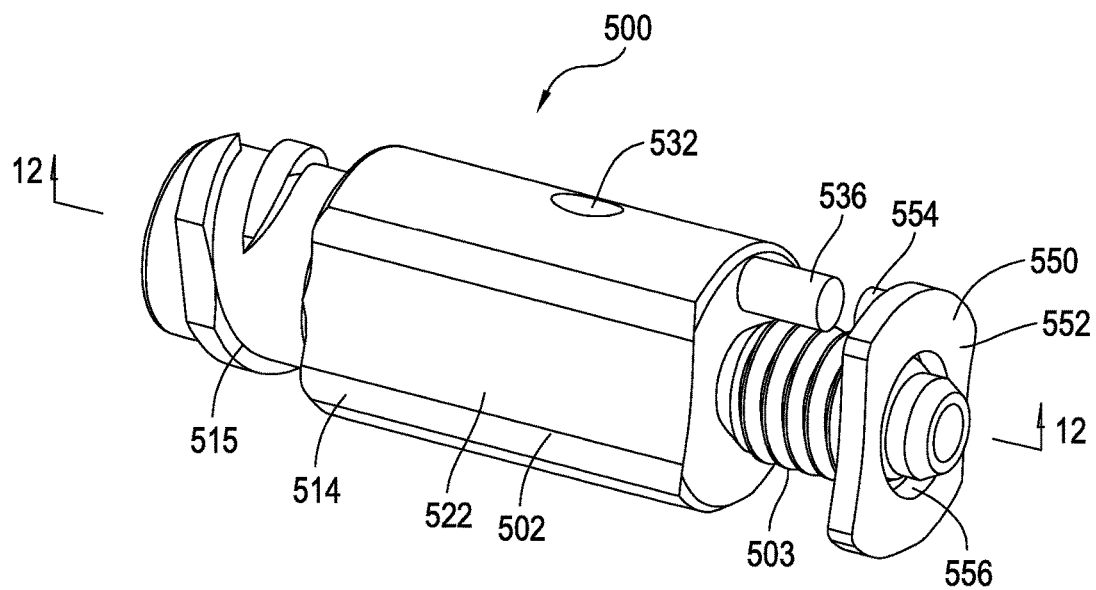
FIG. 11 is a perspective view of a catheter hub in an open position.

FIGS. 1 through 4 illustrate one non-limiting example of a catheter hub according to one embodiment of the present disclosure. FIGS. 5 through 7 show a second non-limiting example of a catheter hub according to a second embodiment of the present disclosure. FIG. 8 illustrates a third non-limiting example of a catheter hub according to another embodiment of the present disclosure. FIGS. 9 and 10 illustrate a fourth non-limiting example of a catheter hub according to another embodiment of the present disclosure. FIGS. 11 through 14 illustrate a fifth non-limiting example of a catheter hub according to another embodiment of the present disclosure. As can be appreciated, features of any of these embodiments may be combined into another embodiment or form a new embodiment.

With reference now to FIGS. 1 through 4, there is shown a catheter hub assembly 100 according to one embodiment of the present disclosure. In this illustrative arrangement, the catheter hub assembly 100 includes a hub body 102 that is configured to engage with a proximal end of a catheter tube (not illustrated) to form a catheter system. The hub body 102 also includes a luer lock end 115 that is configured for attachment to a drainage collection system. The catheter hub assembly 100 includes a locking arm 108 that is configured for attachment to the hub body 102 to clamp a suture or a tension member 110 therebetween. However, the catheter hub assembly 100 may not include the locking arm 108 in another form or the locking arm 108 may be removable from the catheter hub assembly 100. The catheter hub assembly 100 includes a sealing element 136 that can be pierced with a thin medical device or the tension member 110 wherein the sealing element 136 seals an aperture 132 of the hub body 102. The sealing element 136 enables access to a fluid passageway 116 and a patient's vasculature or internal body when a medical device or the tension member 110 passes through the sealing element 136 and into the fluid passageway 116. The sealing element 136 and aperture 132 provides additional access to the fluid passageway 116 over the access provided at a proximal end 114 of the hub body 102 without disconnecting a catheter tube attached to the proximal end 114 and without blocking the proximal end 114. Additionally, the catheter hub assembly 100 can include one or more additional sealing elements positioned in one or more additional apertures in the hub body 102 (similar to sealing element 136 that seals aperture 132). The additional sealing elements positioned in the apertures enable additional lumen access to the fluid passageway 116. For example, a first aperture and corresponding sealing element can be spaced a distance from a second aperture and corresponding sealing element on the hub body 102. For example, aperture 132 is located on an upper body portion 120 and a second aperture similar to aperture 132 can be located on a lower body portion 118 to provide two separate lumens and two fluid passageways. Additionally, the fluid passageway 116 can include one or more additional lumens or passageways such that the first aperture opens to a first fluid passageway and a second aperture opens to a second fluid passageway wherein the first fluid passageway is separate and distinct from the second fluid passageway. Additional apertures and sealing elements can be positioned on the hub body 102 and additional fluid passageways can be positioned in the hub body 102. A single aperture will join with a single fluid passageway to allow separate access to each lumen in the catheter. Alternatively, a single aperture and corresponding sealing element can allow access to multiple fluid passageways and lumens in a catheter.

The illustrated hub body 102 extends along a longitudinal axis L in a substantially cylindrical fashion between a distal end 112 and a proximal end 114. A fluid passageway 116 is configured to receive a portion of the tension member 110, and enable fluid, and/or gasses to pass therethrough. The fluid passageway 116 is substantially cylindrical in cross-sectional shape; however, other shapes or configurations for the cross section are within the scope of this application. One example includes the fluid passageway 116 being tapered cylindrically along its length.

The hub body 102 also includes a lower body portion 118 opposite an upper body portion 120 and a right face 122 opposite a left face 124 wherein the lower and upper body portions 118 and 120 and the right and left faces 122 and 124 span between the distal and the proximal ends 112 and 114, respectively. Generally, the lower body portion 118 has a substantially smooth outer surface. Each of the right and left faces 122 and 124 include a pair of first recesses 125 positioned closer to the distal end 112 and a pair of second recesses 126 positioned closer to the proximal end 114. The first recesses 125 are each configured to receive and retain a first nub on a distal locking arm portion 129 of the locking arm 108 to releasably lock the distal locking arm portion 129 of the locking arm 108 with the hub body 102. As such, the distal locking arm portion 129 of the locking arm 108 is pressed firmly against the upper body portion 120, an aperture 132 therein, the sealing element 136 positioned in the aperture 132, and the tension member 110 to maintain the tension member 110 centered along the upper body portion 120 of the hub body 102. The second recesses 126 are each configured to receive and retain a second nub 137 from a proximal locking arm portion 131 of the locking arm 108 to releasably lock the proximal locking arm portion 131 of the locking arm 108 with the hub body 102. As such, the proximal locking arm portion 131 of the locking arm 108 is pressed firmly against the upper body portion 120 and the tension member 110 is locked in between. The first recesses 125 and the second recesses 126 have a similar triangular shape however, other embodiments can have a different shape or the shape of the first recesses 125 may be different from the shape of the second recesses 126. Other embodiments of the first recesses 125 and the second recesses 126 can include the first recesses 125 or the second recesses 126 in a stacked or a staggered configuration and corresponding arrangement and number of first nubs and second nubs 137 are included on the locking arm 108. The locking arm 108 is flexible or bendable about a joint 164 which enables the first nubs on the distal locking arm portion 129 to be retained in the first recesses 125 independently of the second nubs 137 on the proximal locking arm portion 131 of locking arm 108 that are retained in the second recesses 126. In other words, either or both of the distal locking arm portion 129 and the proximal locking arm portion 131 can be retained with first and the second recesses 125 and 126, respectively, as desired.

The upper body portion 120 includes a first ridge 130 adjacent a distal end 112, a distal portion 127 adjacent to the first ridge 130 and opposite a proximal portion 128 with a second ridge 133 between the distal portion 127 and the proximal portion 128 to separate these portions, and a third ridge 135 positioned between the proximal portion 128 and the proximal end 114. The distal portion 127 is substantially smooth and has a curvature and configuration that complements or corresponds to the inner surface of the distal locking arm portion 129 of the locking arm 108 to form a flush fit between the locking arm 108 and the distal portion 127. The distal portion 127 also defines an aperture 132 that spans from the fluid passageway 116 to an exterior surface 134 of the distal portion 127.

Aperture 132 is sized to receive a sealing element 136. The aperture 132 includes a cylindrical interior shaft portion 138 that engages the fluid passageway 116. The aperture 132 also includes an exterior shaft portion 140 that engages the exterior surface 134. The aperture 132 includes a transition shaft portion 142 positioned between and spanning from the interior shaft portion 138 to the exterior shaft portion 140. In this embodiment, the exterior shaft portion 140 has the largest diameter, the interior shaft portion 138 has the smallest diameter, and the transition shaft portion 142 has a diameter that increases in size from the interior shaft portion 138 to the exterior shaft portion 140. The exterior shaft portion 140 truncates as it intersects the exterior surface 134. The interior shaft portion 138 has a constant diameter along its length. The interior shaft portion 138 and the exterior shaft portion 140 may taper or vary their diameters along their respective lengths. In any form, the transition shaft portion 142 is sized and configured to span between the interior shaft portion 138 and the exterior shaft portion 140. In one embodiment, the exterior shaft portion 140 has a diameter of about 0.080 inches and a maximum length of about 0.10 inches, the interior shaft portion 138 has a diameter of about 0.049 inches and a length of about 0.10 inches, and both of the exterior shaft portion 140 and the interior shaft portion 138 taper in diameter along their respective lengths. Other embodiments of the aperture 132 can have different diameters, shapes, and lengths for the exterior shaft portion 140, the interior shaft portion 138, and the transition shaft portion 142. The shape of aperture 132 may vary depending on the intended use of the catheter hub assembly 100 or the size and shape of the device that will go through the sealing element 136.

The exterior shaft portion 140 has a diameter proportioned to the diameter of the interior shaft portion 138 to receive a softer grade of silicone for sealing element 136 to self-seal under pressure. The interior shaft portion 138 must be small enough to contain the sealing element 136 but large enough to allow a suture, a wire, the tension member 110, a needle, or other instrument to pass through. In one embodiment, the ratio of exterior shaft portion 140 to the interior shaft portion 138 is 2:1 which is very suitable for a thin suture and semi-soft silicone for the sealing element 136.

The proximal portion 128 of the upper body portion 120 includes a plurality of hub serrated teeth 146 that are sized and arranged to engage a corresponding number of a plurality of locking arm serrated teeth 150 on proximal locking arm portion 131 of the locking arm 108. In the illustrated embodiment, each of the plurality of hub serrated teeth 146 has a substantially triangular shape. However, other configurations of the plurality of hub serrated teeth 146 can include rectangular, curved, or polygonal shape. Additionally the plurality of hub serrated teeth 146 and the plurality of locking arm serrated teeth 150 are configured to retain the tension member 110 between them and stop movement of the tension member 110 when proximal locking arm portion 131 of the locking arm 108 is in the locked or closed position as illustrated in FIG. 1.

The first ridge 130 is a raised surface that spans around the perimeter of the hub body 102. In the illustrated embodiment, the first ridge 130 forms a ring around the hub body 102. The first ridge 130 may have other shapes such as rectangular, square, or a polygonal shape.

The second ridge 133 and the third ridge 135 are substantially similar in the illustrated embodiment; however, the second ridge 133 has a diameter that is slightly smaller than a diameter of the first ridge 130 and the third ridge 135. In other embodiments the second ridge 133 is the same size as either or both of the first ridge 130 or the third ridge 135. The second ridge 133 is a raised surface that spans laterally across the upper body portion 120. In the illustrated embodiment, the second ridge 133 forms a raised ring shape. The second ridge 133 also includes a joint or groove 158 that is located along a centerline of the plurality of hub serrated teeth 146 and the centerline of the upper body portion 120 wherein the groove 158 is sized to receive the tension member 110 therein. As such, the groove 158 centers or aligns the tension member 110 towards a centerline of the plurality of hub serrated teeth 146 and along the longitudinal axis L.

The third ridge 135 is positioned between the proximal portion 128 and the proximal end 114. The third ridge 135 is a raised surface that spans laterally across the upper body portion 120. In the illustrated embodiment, the third ridge 135 forms a raised circular shape that spans laterally across the upper body portion 120. The third ridge 135 can have an alternate shape such as a nub, rectangular, square, or polygonal shape. The third ridge 135 includes a joint or groove 159 that is located along a centerline of the plurality of hub serrated teeth 146 wherein the groove 159 is sized to receive the tension member 110 therein. As such, the groove 159 centers or aligns the tension member 110 along the centerline of the plurality of hub serrated teeth 146 and the longitudinal axis L when the distal locking arm portion 129 of the locking arm 108 is locked with or in contact with the hub body 102.

The sealing element 136 is sized to sealingly engage the aperture 132 to provide a self-sealing non-protruding access valve that is sealed within the hub body 102. The sealing element 136 allows a needle, a suture, tension member 110, wire guide, or other similarly thin medical device to pass through the sealing element 136 to gain access to the fluid passageway 116 and a patient's internal vasculature or body. The sealing element 136 is made of silicon or other self-sealing material and beneficially self-seals when the sealing element 136 is punctured by a medical device, suture, or tension member 110 and does not allow fluid and silicone to escape through the sealing element 136 after being punctured. The sealing element 136 when punctured, displaces itself and does not crack or become displaced from the aperture 132. The sealing element 136 may be made of silicone, thermoplastic, or polyisoprene material. The silicone for sealing element 136 may be formed from different durometers depending on the size of the aperture 132. Typically for a larger sized aperture 132, the durometer of the silicone will be lower which forms softer silicone and a softer sealing element 136. Typically for a smaller sized aperture 132, the durometer of the silicone will be higher which forms a harder silicone for the sealing element 136. Example ranges of the durometer of silicone for sealing element 136 are from about 30 Shore A to about 100 Shore A on the Shore Hardness Scale. Pigment or color can be added to the silicone when manufacturing the sealing element 136 to distinguish the sealing element 136 from the hub body 102. The silicone may be transparent or milky after molding.

The sealing element 136 includes a cylindrical interior shaft member 151 that corresponds in diameter to the cylindrical interior shaft portion 138 such that the interior shaft member 151 fits snugly in the interior shaft portion 138. The interior shaft member 151 has a length that is about the same or less than a length of the interior shaft portion 138. The interior shaft member 151 has a length that does not extend into the fluid passageway 116. The sealing element 136 includes a cylindrical exterior shaft member 152 that corresponds in diameter to the exterior shaft portion 140. The exterior shaft member 152 fits snugly in the exterior shaft portion 140. The exterior shaft member 152 has a length that engages the exterior surface 134. In other forms, the exterior shaft member 152 has a length that may extend above the exterior surface 134. The sealing element 136 includes a transition shaft member 154 that corresponds in diameter to the transition shaft portion 142 wherein the transition shaft member 154 spans from the interior shaft member 151 to the exterior shaft member 152. The transition shaft member 154 fits snugly in the transition shaft portion 142.

Turning now to the locking arm 108, the locking arm 108 includes an exterior surface 160 opposite an interior surface 162, and has a length that includes a distal locking arm portion 129 adjacent a proximal locking arm portion 131 with a joint 164 therebetween about which either the distal or proximal locking arm portions 129 and 131 can rotate or bend. The locking arm 108 forms a U-shape wherein the interior surface 162 is configured to enclose and substantially cover the upper body portion 120, the sealing element 136, the right face 122, and the left face 124 of the hub body 102.

The distal locking arm portion 129 includes a pair of first nubs on the interior surface 162 of both a left side 168 and a right side 170 of the locking arm 108 to respectively engage the pair of first recesses 125 to releasably lock the distal locking arm portion 129 of the locking arm 108 with the hub body 102. The pair of first nubs and the pair of first recesses 125 have complementary shapes such that one of the first nubs is retained in one of the first recesses 125. The pair of first nubs and the pair of first recesses 125 have a complementary triangular shape but may be shaped differently in alternative embodiments. In an assembled and locked configuration, the distal locking arm portion 129 of the locking arm 108 is pressed firmly against the upper body portion 120, the aperture 132 therein, the sealing element 136, and the tension member 110 to maintain the tension member 110 in a centered position along the longitudinal axis L. The distal locking arm portion 129 includes a hole 165 that is sized and positioned to receive the tension member 110 there through. Hole 165 is an elongate oval or slot shape that allows a surgeon to pull a portion of the tension member 110 through it to tighten the tension member 110 as needed.

The proximal locking arm portion 131 includes a pair of second nubs 137 on the interior surface 162 of both a left side 168 and a right side 170 of the locking arm 108 to respectively engage the pair of second recesses 126 to releasably lock the proximal locking arm portion 131 of the locking arm 108 with the hub body 102. Each of the pair of second recesses 126 is configured to receive and retain one of a pair of second nubs 137 from a proximal locking arm portion 131 of the locking arm 108 to releasably lock the proximal locking arm portion 131 of the locking arm 108 with the hub body 102. In a locked or closed position, the proximal locking arm portion 131 of the locking arm 108 is pressed firmly against the upper body portion 120 and the corresponding portion of the tension member 110 is locked there between and restrained from movement. In an unlocked or open position, the proximal locking arm portion 131 of the locking arm 108 is rotated about the joint 164 away from the upper body portion 120 such that the tension member 110 can freely move and is no longer restrained. The proximal locking arm portion 131 defines a recess 169 that may be sized to enable a user to more easily grasp the proximal locking arm portion 131 such that the recess 169 is sized to receive a finger or thumb to rotate or move the proximal locking arm portion 131 about the joint 164.

The components of hub assembly 100, including the hub body 102 and the locking arm 108, may be manufactured by injection molding using a variety of plastics, including acrylonitrile butadiene styrene (ABS), polybutylene terephthalate (PBT) plastic, and/or polypropylene plastic, or other techniques. In other embodiments, the locking arm 108 and the hub body 102 may be configured differently. Regarding the suture or tension member 110, while suture material in particular will be useful in certain embodiments, a variety of other elongate materials and objects capable of being anchored can be used as an alternative to, or in addition, to suture material. These include various types of cords, filaments, chains, strings, wires and other similar objects having relatively slender profiles for extending through patient tissue.

With reference now to FIGS. 5 through 7, there is shown a catheter hub assembly 200 according to the present disclosure. The catheter hub assembly 200 is similar to catheter hub assembly 100 therefore similar details will not be discussed. The catheter hub assembly 200 includes a hub body 202 that is configured to engage with a proximal end of a catheter tube (not illustrated) to form a catheter system. The catheter hub assembly 200 includes a locking arm 208 that is configured for attachment to the hub body 202 to clamp a suture or a tension member 210 between the hub body 202 and the locking arm 208. However, the catheter hub assembly 200 may not include the locking arm 208 in another form or the locking arm 208 may be removable from the catheter hub assembly 200. The catheter hub assembly 200 also includes a sealing element 236 in an aperture 232 of the hub body 202. The sealing element 236 enables access to a fluid passageway 216 and a patient's vasculature or internal body when a medical device or the tension member 210 passes through the sealing element 236 and into the fluid passageway 216. The sealing element 236 and aperture 232 provide additional access to the fluid passageway 216 over the access provided at a proximal end 214 of the hub body 202 without disconnecting a catheter tube attached to the proximal end 214 and without blocking the proximal end 214.

The hub body 202 is similar to hub body 102 therefore similar features will not be described again. The hub body 202 includes a lower body portion 218 opposite an upper body portion 220, and a right face opposite a left face wherein the lower and upper body portions 218 and 220 and the right and left faces span between a distal end 212 and a proximal end 214. Each of the right and left faces include a single recess positioned closer to the distal end 212 and a single recess positioned closer to the proximal end 114. The recesses positioned on the hub body 202 closer to the distal end 212 are similar to the first recesses 125 and are configured to receive and retain a nub 266 on a distal locking arm portion 229 of the locking arm 208 to releasably lock the distal locking arm portion 229 of the locking arm 208 with the hub body 202. As such, the distal locking arm portion 229 of the locking arm 208 is pressed firmly against the upper body portion 220, an aperture 232 therein, the sealing element 236 positioned in the aperture 232, and the tension member 210 to maintain the tension member 210 centered along the upper body portion 220 of the hub body 202. The recesses positioned on the hub body 202 closer to the proximal end 214 are similar to the second recesses 126 and are configured to receive and retain a nub 237 from a proximal locking arm portion 231 of the locking arm 208 to releasably lock the proximal locking arm portion 231 of the locking arm 208 with the hub body 202. As such, the proximal locking arm portion 231 of the locking arm 208 is pressed firmly against the upper body portion 220 and the tension member 210 is locked in between. The locking arm 208 is flexible or bendable about a joint 264 which enables the nub 266 on the distal locking arm portion 229 to be retained in the recess near the distal end 212 independently of the nub 237 on the proximal locking arm portion 231 of locking arm 208 that is retained in the recess near the proximal end 214. In other words, either or both of the distal locking arm portion 229 and the proximal locking arm portion 231 can be retained with the recesses near the distal end 212 and the proximal end 214, respectively, as desired.

The upper body portion 220 includes a first ridge 230 near the distal end 212, a distal portion 227 adjacent to the first ridge 230 and opposite a proximal portion 228 with a second ridge 233 between the distal portion 227 and the proximal portion 228 to separate these portions, and a third ridge 235 positioned between the proximal portion 228 and the proximal end 214. The distal portion 227 is substantially smooth and has a curvature and configuration that complements or corresponds to the inner surface of the distal locking arm portion 229 of the locking arm 208 to form a flush fit between the locking arm 208 and the distal portion 227. The distal portion 227 also defines an aperture 232 that spans from the fluid passageway 216 to an exterior surface 234 of the distal portion 227. The distal portion 227 includes a raised surface 239 that spans from the aperture 232 to the first ridge 230.

Aperture 232 is sized to receive and retain a sealing element 236. The aperture 232 includes a cylindrical interior shaft portion 238 that engages the fluid passageway 216. The aperture 232 also includes an exterior shaft portion 240 that engages the exterior surface 234 and the raised surface 239. The aperture 232 includes a transition shaft portion 242 positioned between and spanning from the interior shaft portion 238 to the exterior shaft portion 240. In this embodiment, the exterior shaft portion 240 has the largest diameter, the interior shaft portion 238 has the smallest diameter, and the transition shaft portion 242 has a diameter that increases in size from the interior shaft portion 238 to the exterior shaft portion 240. The interior shaft portion 238 and the exterior shaft portion 240 each have a constant diameter along their respective lengths. However, the interior shaft portion 238 and the exterior shaft portion 240 may taper or vary their diameters along their respective lengths. In any form, the transition shaft portion 242 is sized and configured to span between the interior shaft portion 238 and the exterior shaft portion 240. Other embodiments of the aperture 232 can have different diameters and lengths for the exterior shaft portion 240, the interior shaft portion 238, and the transition shaft portion 242.

Similarly to the proximal portion 128, the proximal portion 228 of the upper body portion 220 includes a plurality of hub serrated teeth 246 that are sized and arranged to engage a corresponding number of a plurality of locking arm serrated teeth 250 on proximal locking arm portion 231 of the locking arm 208. The plurality of hub serrated teeth 246 and the plurality of locking arm serrated teeth 250 are configured to retain the tension member 210 between them and stop movement of the tension member 210 when proximal locking arm portion 231 of the locking arm 208 is in the locked or closed position as illustrated in FIG. 5. In the unlocked or open position as illustrated in FIG. 6, the tension member 210 may be moved through the sealing element 236.

The first ridge 230 is a raised surface that spans around the perimeter of the hub body 202. In the illustrated embodiment, the first ridge 230 forms a ring around the hub body 202. Alternatively, the first ridge 230 may form a ring that spans around a portion of the perimeter of the hub body 202. In other forms, the first ridge 230 is not present such that the raised surface 239 extends from the aperture 232. The raised surface 239 spans from the aperture 232 to the first ridge 230. The raised surface 239 is configured to retain the sealing element 236 in the aperture 232.

The second ridge 233 is substantially similar to the second ridge 133, and the third ridge 235 is substantially similar to the third ridge 135.

The sealing element 236 is sized to sealingly engage the aperture 232 to provide a self-sealing non-protruding access valve that is sealed within the hub body 202. The sealing element 236 allows a needle, a suture, tension member 210, wire guide, or other similarly thin medical device to pass through the sealing element 236 to gain access to the fluid passageway 216 and a patient's internal vasculature or body. The sealing element 236 is made of silicon or other self-sealing material and beneficially self-seals when the sealing element 236 is punctured by a medical device, suture, or tension member 210. The sealing element 236 includes a cylindrical interior shaft member 251 that corresponds in diameter to the cylindrical interior shaft portion 238 such that the interior shaft member 251 fits snugly in the interior shaft portion 238 to seal the interior shaft portion 238. The interior shaft member 251 has a length that is less than a length of the interior shaft portion 238 but the interior shaft member 251 can extend to the fluid passageway 216. The interior shaft member 251 has a length that does not extend into the fluid passageway 216. The sealing element 236 includes a cylindrical exterior shaft member 252 that corresponds in diameter to the exterior shaft portion 240. The exterior shaft member 252 fits snugly in the exterior shaft portion 240 to seal the exterior shaft portion 240. The exterior shaft member 252 has a length that engages the raised surface 239 and the distal portion 227. The sealing element 236 includes a transition shaft member 254 that corresponds in diameter to the transition shaft portion 242 wherein the transition shaft member 254 spans from the interior shaft member 251 to the exterior shaft member 252. The transition shaft member 254 fits snugly in the transition shaft portion 242 to seal the transition shaft portion 242.

The locking arm 208 is substantially similar to the locking arm 108. The locking arm 208 includes an exterior surface 260 opposite an interior surface 262, and has a length that includes a distal locking arm portion 229 adjacent a proximal locking arm portion 231 with a joint 264 therebetween about which either the distal or proximal locking arm portions 229 and 231 can rotate or bend. The locking arm 208 forms a U-shape wherein the interior surface 262 is configured to enclose and substantially cover the upper body portion 220, the right face, and the left face of the hub body 202.

The distal locking arm portion 229 includes a first nub 266 on the interior surface 262 of both a left side 268 and a right side 270 of the locking arm 208 to respectively engage the right and left faces that include a first recess (not illustrated) positioned closer to the distal end 212. The first nubs 266 are similar to the first nubs on the locking arm 108. The first recesses near the distal end 212 are similar to the first recesses 125. In an assembled and locked configuration, the distal locking arm portion 229 of the locking arm 208 is pressed firmly against the upper body portion 220, the aperture 232 therein, the sealing element 236, and the tension member 210 to maintain the tension member 210 in a centered position along the longitudinal axis L. Additionally, the distal locking arm portion 229 may be flexible to conform to the raised surface 239. The distal locking arm portion 229 includes a hole 265 that is sized and positioned to receive the tension member 210 there through. Hole 265 is an elongate oval or slot shape that allows a surgeon to pull a portion of the tension member 210 through the hole 265 to tighten the tension member 210 as needed.

The proximal locking arm portion 231 includes a second nub 237 on the interior surface 262 of both the left side 268 and the right side 270 of the locking arm 208 to respectively engage the right and left faces of the hub body 202 that include a second recess (not illustrated) positioned closer to the proximal end 214 to releasably lock the proximal locking arm portion 231 of the locking arm 208 with the hub body 202. The second nub 237 is similar to the first nub 266, and the second recess near the proximal end 214 is similar to the second recesses 126. In a locked or closed position, the proximal locking arm portion 231 of the locking arm 208 is pressed firmly against the upper body portion 220 and the corresponding portion of the tension member 210 is locked there between and restrained from movement. In an unlocked or open position, the proximal locking arm portion 231 of the locking arm 208 is rotated about the joint 264 away from the upper body portion 220 such that the tension member 210 can freely move and is no longer restrained. The proximal locking arm portion 231 defines a recess 269 that may be sized to enable a user to more easily grasp the proximal locking arm portion 231 such that the recess 269 is sized to receive a finger or thumb to rotate or move the proximal locking arm portion 231 about the joint 264.

With reference now to FIG. 8, there is shown a catheter hub assembly 300 according to the present disclosure. The catheter hub assembly 300 is similar to catheter hub assembly 200 therefore similar details will not be discussed. The catheter hub assembly 300 does not include a locking arm as the locking arm is not necessary to seal an aperture 332, although a locking arm may be included and attached to a hub body 302 of the catheter hub assembly 300. The catheter hub assembly 300 includes the hub body 302 that is configured to engage with a proximal end of a catheter tube (not illustrated) to form a catheter system. The catheter hub assembly 300 also includes a sealing element 336 in an aperture 332 of the hub body 302. The sealing element 336 enables access to a fluid passageway 316 and a patient's vasculature or internal body when a medical device or a tension member 310 passes through the sealing element 336 and into the fluid passageway 316. The sealing element 336 and aperture 332 provide additional access to the fluid passageway 316 over the access provided at a proximal end 314 of the hub body 302 without disconnecting a catheter tube attached to the proximal end 314 and without blocking the proximal end 314. The fluid passageway 316 may taper from the proximal end 314 to a distal end 312 of the catheter hub assembly 300.

Aperture 332 is sized to receive and retain the sealing element 336. The aperture 332 includes a cylindrical interior shaft portion 338 that engages the fluid passageway 316. The aperture 332 also includes an exterior shaft portion 340 that engages an exterior surface 334 and a raised surface 339. The exterior shaft portion 340 tapers from a smaller diameter at the interior shaft portion 338 to a larger diameter that spans from the exterior surface 334 to the raised surface 339. As such, the exterior shaft portion 340 has a diameter that increases in size from the interior shaft portion 338 to the exterior shaft portion 340. The interior shaft portion 338 has a constant diameter along the length of the interior shaft portion 338. However, the diameter of the interior shaft portion 338 may taper or vary along the length of the interior shaft portion 338. Other embodiments of the aperture 332 can have different diameters and lengths for the exterior shaft portion 340 and the interior shaft portion 338.

The sealing element 336 is sized to sealingly engage the aperture 332 to provide a self-sealing non-protruding access valve that is sealed within the hub body 302. The sealing element 336 allows a needle, a suture, tension member 310, wire guide, or other similarly thin medical device to pass through the sealing element 336 to gain access to the fluid passageway 316 and a patient's internal vasculature or body. The sealing element 336 is made of silicon or other self-sealing material and beneficially self-seals when the sealing element 336 is punctured by a medical device, suture, or tension member 310. The sealing element 336 includes a cylindrical interior shaft member 351 that corresponds in diameter to the cylindrical interior shaft portion 338 such that the interior shaft member 351 fits snugly in the interior shaft portion 338 to seal the interior shaft portion 338. The interior shaft member 351 has a length that is less than a length of the interior shaft portion 338 but the interior shaft member 351 may extend to the fluid passageway 316 in another form. The interior shaft member 351 has a length that does not extend into the fluid passageway 316. The sealing element 336 includes a cylindrical exterior shaft member 352 that corresponds in diameter to the exterior shaft portion 340. The exterior shaft member 352 fits snugly in the exterior shaft portion 340 to seal the exterior shaft portion 340. The exterior shaft member 352 has a length that extends to the raised surface 339 and the exterior surface 334. The exterior shaft member 352 has a diameter that increases from interior shaft member 351 to the opening of the aperture 332 that spans between the raised surface 339 and the exterior surface 334.

With reference now to FIGS. 9 and 10, there is shown a catheter hub assembly 400 according to another embodiment of the present disclosure. In this illustrative arrangement, the catheter hub assembly 400 includes a hub body 402 that is configured to engage with a proximal end of a catheter tube (not illustrated) to form a catheter system. The hub body 402 also includes a luer lock end 415 that is configured for attachment to a drainage collection system. The catheter hub assembly 400 includes a sealing element 436 that can be pierced with a thin medical device or a tension member (not illustrated) wherein the sealing element 436 seals a first aperture 432 and a second aperture 433 of the hub body 402. The sealing element 436 enables access to a fluid passageway 416 and a patient's vasculature or internal body when a medical device or the tension member passes through the sealing element 436 and into the fluid passageway 416. The sealing element 436 and the first aperture 432 provides additional access to the fluid passageway 416 over the access provided at a proximal end 414 of the hub body 402 without disconnecting a catheter tube attached to the proximal end 414 and without blocking the proximal end 414.

The illustrated hub body 402 extends along a longitudinal axis L in a substantially cylindrical fashion between a distal end 412 and a proximal end 414. A fluid passageway 416 is configured to receive a portion of the tension member, and enable fluid, and/or gasses to pass therethrough. The fluid passageway 416 is substantially cylindrical in cross-sectional shape; however, other shapes or configurations for the cross section are within the scope of this application. One example includes the fluid passageway 416 being tapered cylindrically along its length.

The hub body 402 also includes a lower body portion 418 opposite an upper body portion 420 and a right face 422 opposite a left face (not illustrated) wherein the lower and upper body portions 418 and 420, respectively, and the right face 422 and the left face span between the distal and the proximal ends 412 and 414, respectively. Generally, the lower and the upper body portions 418 and 420, respectively, the right face 422 and the left face each have a substantially smooth outer surface.

The upper body portion 420 defines the first aperture 432 that spans from the fluid passageway 416 to an exterior surface 434 of the upper body portion 420. The upper body portion 420 may include additional apertures that extend from the fluid passageway 416 to an exterior surface 434. The additional apertures would be positioned in the hub body 402 and the sealing element 436 is configured such that the sealing element 436 spans across the additional apertures to seal the additional apertures. The upper body portion 420 also defines the second aperture 433 that spans from the distal end 412 through the first aperture 432 and a distance or a portion 435 past the first aperture 432 towards the proximal end 414. As such, the second aperture 433 intersects the first aperture 432 at an acute angle θ as measured relative to the longitudinal axis L. Angle θ ranges from about 10 degrees to about 90 degrees. First aperture 432 is sized to receive the sealing element 436; however, the sealing element 436 travels through the second aperture 433 to span across the first aperture 432. The first aperture 432 is substantially cylindrical and has a constant diameter along its length. Second aperture 433 is sized to receive the sealing element 436 that travels through the second aperture 433. The second aperture 433 is substantially cylindrical and has a constant diameter along its length that corresponds to a diameter of the sealing element 436. Alternatively, the first aperture 432 and the second aperture 433 may taper or vary their diameters along their respective lengths. In one embodiment, the first aperture 432 has a diameter of about 0.080 inches and a maximum length of about 0.10 inches, the second aperture 433 has a diameter of about 0.049 inches and a length of about 0.10 inches. Other embodiments of the first aperture 432 and the second aperture 433 can have different diameters and lengths as long as the first aperture 432 and the second aperture 433 are sized to receive the sealing element 436 as described above.

The first aperture 432 and the second aperture 433 are sized and arranged to receive the sealing element 436 that is made of stiffer silicone as compare to the softer silicone for sealing element 136 in aperture 132. The first aperture 432 and the second aperture 433 are sized and arranged such that a higher pressure (as compared to aperture 132) can be applied to sealing element 436. This application of higher pressure can be beneficial for higher use cases where many needle punctures may be necessary or a wire pulled back and forth repeatedly. The sealing element 436 is sized to sealingly engage the first aperture 432 and the second aperture 433 to provide a self-sealing non-protruding access valve that is sealed within the hub body 402. The sealing element 436 allows a needle, a suture, a tension member, wire guide, or other similarly thin medical device to pass through the sealing element 436 to gain access to the fluid passageway 416 and a patient's internal vasculature or body. The sealing element 436 is made of silicon or other self-sealing material and beneficially self-seals when the sealing element 436 is punctured by a medical device, suture, or tension member. The sealing element 436 corresponds in diameter to the second aperture 433 such that the sealing element 436 fits snugly in the second aperture 433 and into the portion 435 to cover the first aperture 432. As such, the sealing element 436 spans across the first aperture 432 to seal the first aperture 432. The sealing element 436 has a length that is about the same or slightly more than a length of the second aperture 433. The sealing element 436 has a length that extends to the distal end 412.

Although not illustrated in FIGS. 9 and 10, the catheter hub assembly 400 may include a locking arm similarly configured as described above to retain a tension member between the locking arm and the hub body 402. Additionally, the upper body portion 420 of the hub body 402 may include a plurality of hub serrated teeth (described above) that are sized and arranged to engage a corresponding number of a plurality of locking arm serrated teeth (described above) on the locking arm. In this embodiment, the plurality of hub serrated teeth and the plurality of locking arm serrated teeth are configured to retain a tension member between them and stop movement of the tension member when locking arm is in the locked or closed position. The tension member freely moves when the locking arm is in the unlocked or open position.

The components of hub assembly 400, including the hub body 402 and a locking arm, may be manufactured by injection molding using a variety of plastics, including acrylonitrile butadiene styrene (ABS), polybutylene terephthalate (PBT) plastic, and/or polypropylene plastic, or other techniques. In other embodiments, the hub body 402 may be configured differently. Any suture or tension member will be similar to the suture or tension member 110 described above.

With reference now to FIGS. 11 through 14, there is shown a catheter hub assembly 500 according to another embodiment of the present disclosure. The catheter hub assembly 500 is similar to catheter hub assembly 400; therefore, for the sake of brevity similar details will not be described again. The catheter hub assembly 500 includes a locking device 550 which is not illustrated with the catheter hub assembly 400. However, the locking device 550 may be incorporated into the catheter hub assembly 400 as disclosed and described herein.

The catheter hub assembly 500 includes a hub body 502 wherein the hub body 502 includes a catheter tube end 503 to engage with a proximal end of a catheter tube (not illustrated) to form a catheter system. The catheter tube end 503 is configured to receive the locking device 550. The catheter tube end 503 has an outer surface that includes a plurality of ridges and grooves but alternatively the outer surface may be smooth. The hub body 502 also includes a luer lock end 515 that is configured for attachment to a drainage collection system. The catheter hub assembly 500 includes a sealing element 536 that may be pierced with a thin medical device or a tension member (not illustrated) wherein the sealing element 536 seals a first aperture 532 and seals a second aperture 533 of the hub body 502. The sealing element 536 enables access to a fluid passageway 516 and a patient's vasculature or internal body when a medical device or the tension member passes through the sealing element 536 and into the fluid passageway 516. The sealing element 536 and the first aperture 532 provides additional access to the fluid passageway 516 over the access provided at a proximal end 514 of the hub body 502 without disconnecting a catheter tube attached to the luer lock end 515 and the proximal end 514 and without blocking the proximal end 514 of the hub body 502.

Additionally, the catheter hub assembly 500 can include one or more additional first apertures similar to first aperture 532 and a corresponding number of second apertures similar to second aperture 533. These additional first and second apertures and sealing elements (not illustrated) can be positioned around the circumference of the hub body 502. For each of first and corresponding second apertures, there will be a single sealing element similar to sealing element 536. In one embodiment, there will be a total of four first apertures, four second apertures, and four sealing elements spaced about equidistant from each other around the circumference of the hub body 502.

The hub body 502 extends along a longitudinal axis L in a substantially cylindrical fashion between a distal end 512 and a proximal end 514. The hub body 502 also includes a lower body portion 518 opposite an upper body portion 520 and a right face 522 opposite a left face (not illustrated) wherein the lower and upper body portions 518 and 520, respectively, and the right face 522 and the left face span between the distal and the proximal ends 512 and 514, respectively.

Although not illustrated in FIGS. 11 through 14, the catheter hub assembly 500 may include a locking arm similarly configured as described above to retain a tension member between the locking arm and the hub body 502. Additionally, the upper body portion 520 of the hub body 502 may include a plurality of hub serrated teeth (described above) that are sized and arranged to engage a corresponding number of a plurality of locking arm serrated teeth (described above) on the locking arm. In this form, the plurality of hub serrated teeth and the plurality of locking arm serrated teeth are configured to retain a tension member between them and stop movement of the tension member when locking arm is in the locked or closed position. The tension member freely moves when the locking arm is in the unlocked or open position.

Turning now to the locking device 550, the locking device 550 is configured to engage the sealing element 536 and the locking device 550 is configured to attach to the catheter tube end 503. The locking device 550 has a body 552 and a nub 554 and an opening 556 within the body 552 that is sized to receive the catheter tube end 503. The nub 554 extends towards the sealing element 536 when the locking device 550 is assembled with the hub body 502. The body 552 may be any shape; however, in the illustrated embodiment the body 552 is substantially circular in shape and corresponds to the circumference of the hub body 502. The body 552 has a thickness or width that enables a user or mechanical device to grasp and engage the body 552 to press the body 552 against the sealing element 536. In this arrangement, the locking device 550 has a greater stiffness than the sealing element 536 to enable the locking device 550 to press against the sealing element 536 and compress the sealing element 536. The sealing element 536 is compressible by the body 552 and the nub 554. The nub 554 has about the same size diameter as the sealing element 536 to engage the sealing element 536 and compress the sealing element 536 into the second aperture 533 and towards the portion 535. The nub 554 may be made of the same material as the body 552 or a different material. Alternatively, the locking device 550 may not include the nub 554 and instead the sealing element 536 includes a stiffer portion such as a nub wherein the nub is positioned closer to the distal end 512 to directly contact the sealing element 536.

In the embodiments that include additional first and second apertures and sealing elements, the locking device 550 can include additional nubs similar to nub 554 configured and positioned to engage the additional sealing elements. The additional nubs can also engage and compress the sealing elements.

The additional first apertures provide more access points to the fluid passageway 516. Additional access points can be beneficial in that repeated sticks by a needle or other device may damage the sealing element and the corresponding access point may be damaged. Instead of removing the catheter hub assembly 500 due to a damaged access point and sealing element, a practitioner can use a second access point on the same catheter hub assembly 500, thereby maintaining the catheter hub assembly 500 in a patient. Multiple first and second apertures and sealing elements provide additional access points if one of the sealing elements is damaged by a medical instrument.

The opening 556 of the body 552 may include a plurality of threads configured to engage with a plurality of threads on the catheter tube end 503. In this form, the body 552 is rotatable about the catheter tube end 503 to press against the sealing element 536. Alternatively, the opening 556 in the body 552 is smooth and simply slides over the catheter tube end 503 to press against the sealing element 536. The nub 554 and the body 552 are configured to engage and attach to the proximal end 512 of the hub body 502 to hold the locking device 550 in a locked configuration with the hub body 502 and thereby compress the sealing element 536. The sealing element 536 may be compressed different amounts depending on the amount of pressure applied by the locking device 550 and durometer of the silicone material for the sealing element 536.

Figure 12:
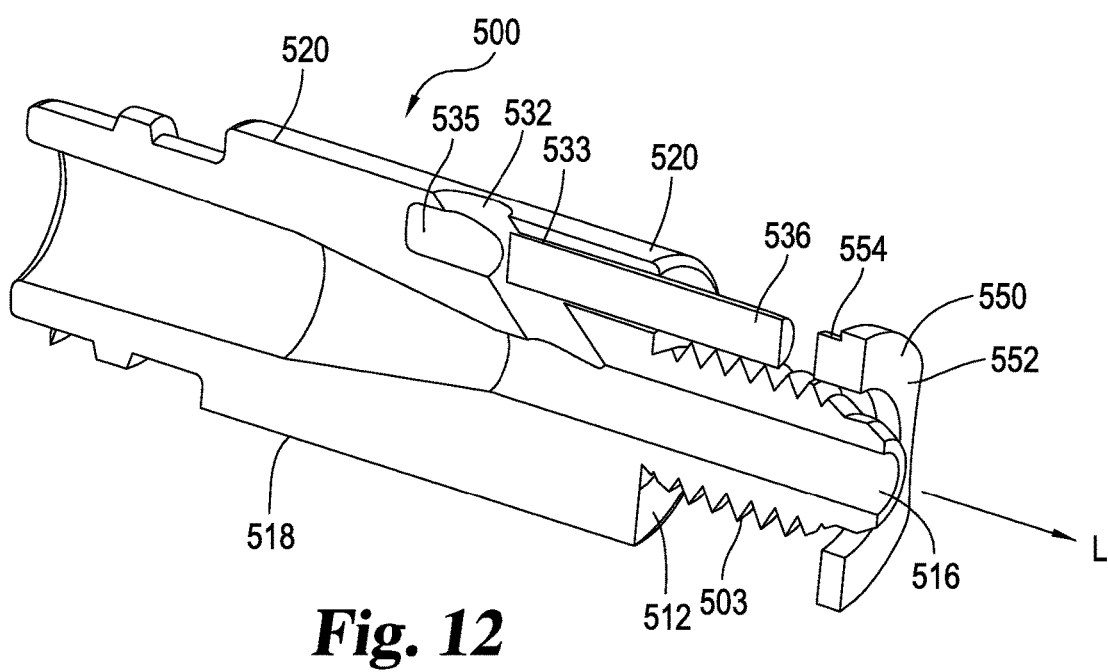
FIG. 12 is a cross-sectional view of the catheter hub of FIG. 11.
Figure 13:
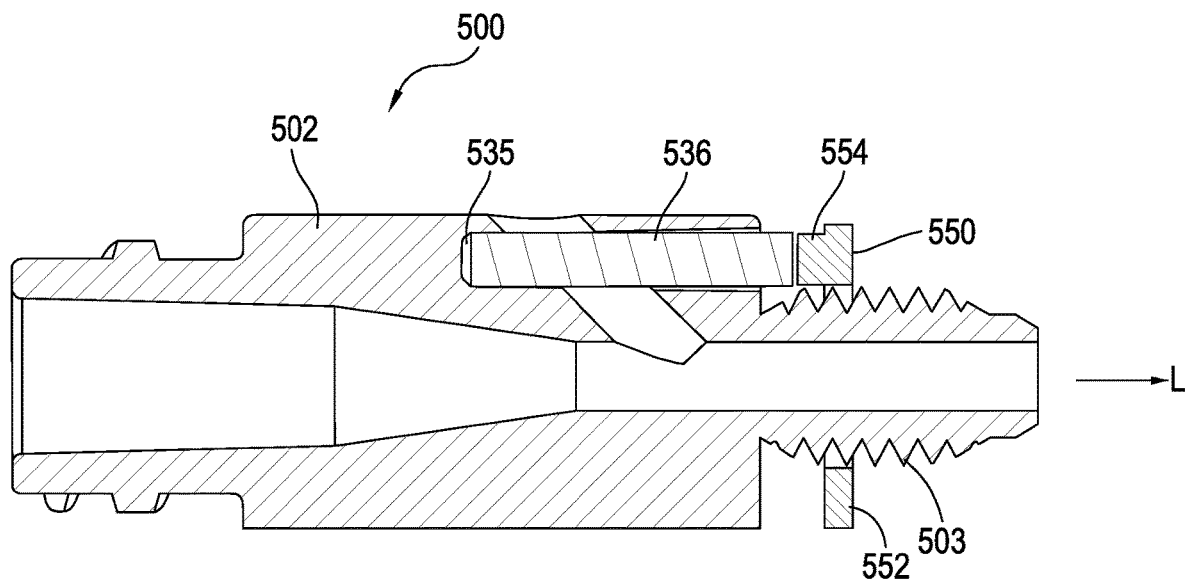
FIG. 13 is a cross-sectional view of the catheter hub of FIG. 11.
Figure 14:
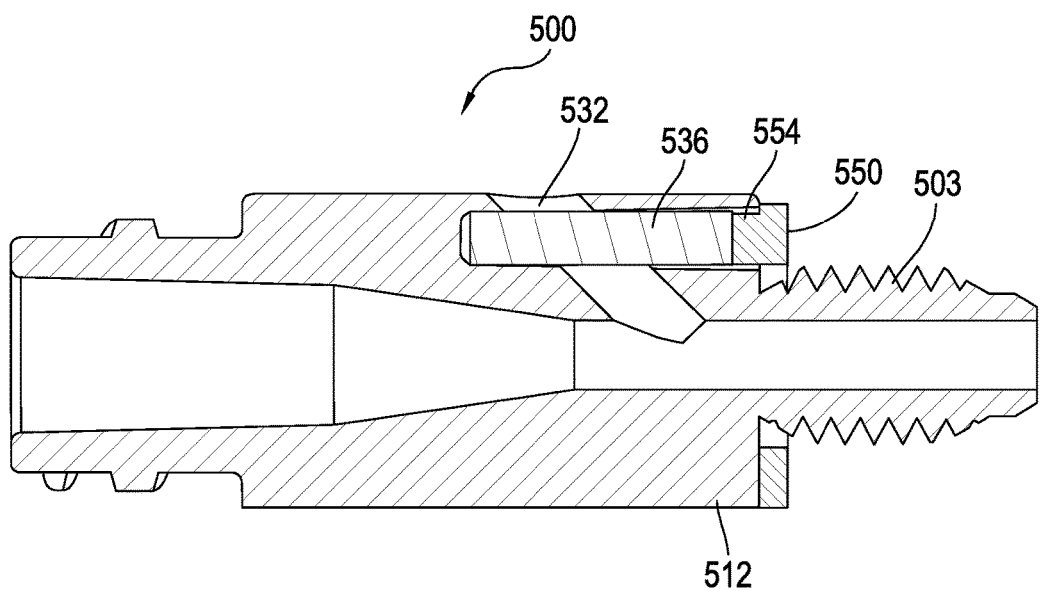
FIG. 14 is a cross-sectional view of the catheter hub of FIG. 11 in a closed position.

Illustrated in FIG. 12, is an initial uncompressed configuration of the sealing element 536 wherein the locking device 550 does not contact the sealing element 536 and the locking device 550 is positioned a distance from the sealing element 536. In FIG. 13, is a semi-compressed configuration of the sealing element 536 wherein the locking device 550 contacts the sealing element 536 and compresses the sealing element 536 into the portion 535 a small amount; however, the locking device 550 is not locked with the hub body 502. In a semi-compressed configuration, a portion of the sealing element 536 may extend out of the second aperture 533 or the sealing element 536 will be fully contained within the second aperture 533. In FIG. 14 is a fully compressed configuration of the sealing element 536 wherein the locking device 550 contacts the sealing element 536 and fully compresses the sealing element 536 into the portion 535 and the second aperture 533. In a fully compressed configuration, the sealing element 536 does not extend out of the second aperture 533 but is fully contained within the second aperture 533. In this configuration, the locking device 550 is locked with the hub body 502. In a fully compressed and locked configuration, the body 552 contacts the proximal end 512 of the hub body 502. The nub 554 and the body 552 are also configured to disengage and unlock from the hub body 502 as desired by the user.

In one form, the catheter hub of the application may be used as follows. Drainage and insertion sites are selected and prepared using appropriate known techniques and a guidewire is inserted into the drainage site. This description describes the "over-the-guidewire" introduction technique. Some physicians also use a "direct puncture" technique in some circumstances. This disclosure is equally useful when performing the direct puncture technique where a trocar is used in place of the guidewire. The catheter hub is identical for both catheter introduction methods.

A catheter in accordance with FIG. 1 (or otherwise in accordance with this disclosure or any other Figures) is provided with catheter hub assembly 100. A cannula (not shown) is then inserted into tube (not shown) of the catheter to maintain the distal end of the tube in a straight configuration so that the catheter may be passed over the previously emplaced guidewire into the drainage site while monitoring using non-invasive imaging such as fluoroscopy, CT (computed tomography) or ultrasound to ensure that the proximal end is properly positioned within the cavity. The proximal end of the catheter including the catheter hub will be outside of the patient's body close to the skin surface at the entry point into the body. At this point, the cannula and guidewire are removed.

When the cannula is removed, a restraining portion of tube curls into its preformed unstressed end of the tubular member configuration. The physician then pulls upon tension member 110 to remove any slack and optionally to further curl the end of the tubular member. Locking arm 108 is then moved or rotated to its locked position (FIG. 1), to maintain the plurality of locking arm serrated teeth 150 in engagement with the plurality of hub serrated teeth 146 on the hub body 102 thereby trapping the suture or tension member 110 between the two toothed surfaces. As discussed above, the locking arm 108 may be removed from the catheter hub assembly 100 in other medical situations as the locking arm 108 is not required to seal the aperture 132. The sealing element 136 continuously seals the aperture 132 and seals around the tension member 110 or other medical device that may pass through the sealing element 136. As such, the sealing element 136 self-seals the aperture 132 and around any medical device or tension member 110 that passes therethrough. In the situation that the tension member 110 is used, the suture or tension member 110 can be simply cut close to the hub body 102 after the device is locked. The luer lock end 115 is then attached to an appropriate drainage collection system and fluid is drained as appropriate. Once the drainage procedure is completed and the catheter is to be removed, the drainage catheter hub is disconnected from the catheter. Locking arm 108 is then rotated to an unlocked position to release the tension member 110. This rotational movement releases the locking arm 108 and the catheter may now be removed from the cavity. A like procedure can be used when the drainage catheter hub is to be used for feeding purposes.

Any or all of the components described herein can be provided in a sterile pack for providing necessary parts, or a variety of parts, to a surgeon. For example, one or more predetermined types or sizes of catheters pre-engaged with a variety of drainage catheter hubs may be provided in a single sterile package or kit. A surgeon can choose the sizes or types of components he or she wishes to use during surgery. Alternatively, sterile kits containing predetermined sizes or types of components may be provided. Packages or kits of the components described herein can include additional devices or tools which may be useful in the particular medical procedure being performed.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A catheter hub for use with a catheter and a tension member for tensioning a distal end region of the catheter, the catheter hub comprising:
a hub body defining a fluid passageway in communication with an aperture, the hub body adapted for attachment to the catheter, the fluid passageway and the catheter aligned for fluid flow therethrough, the aperture extending from and communicating with the fluid passageway to an exterior surface of the hub body;
a sealing element configured to receive the tension member therethrough, the sealing element sized for and positioned in the aperture, wherein the sealing element and the aperture each have a corresponding complementary shape to form a fluid-tight seal between the sealing element and the aperture, the sealing element being fully retained within the aperture;
a locking arm attached to the hub body having a proximal portion and a distal portion, the distal portion positioned to cover the aperture;
a hole defined in the distal portion of the locking arm and sized and positioned to receive the tension member therethrough;
wherein the hub body has a first side face defining a first recess and a second side face defining a second recess;
wherein the proximal portion of the locking arm has an interior surface defining a first nub receivable in the first recess and a second nub receivable in the second recess; and
wherein the hub body and the locking arm are convertible between a releasably locked position in which the first nub and the second nub are received in the first recess and the second recess, respectively, and an unlocked position in which the first nub and the second nub are removed from the first recess and the second recess, respectively.

2. The catheter hub according to claim 1, wherein the aperture includes a transition shaft portion that spans between an interior shaft portion and an exterior shaft portion, the interior shaft portion configured to engage the fluid passageway, the exterior shaft portion configured to engage an exterior surface of the hub body; and
the sealing element includes a transition shaft member that spans between an interior shaft member and an exterior shaft member wherein the transition shaft member is sized to fill the transition shaft portion, the interior shaft member is sized to fill the interior shaft portion, the exterior shaft member is sized to fill the exterior shaft portion.

3. The catheter hub according to claim 2, wherein a diameter of the interior shaft portion is smaller than a diameter of the exterior shaft portion, and a diameter of the transition shaft portion tapers from the exterior shaft portion to the interior shaft portion.

4. The catheter hub according to claim 1, wherein the sealing element is made of silicone, thermoplastic, or polyisoprene material, or a combination of these materials.

5. The catheter hub according to claim 1, further comprising:
a plurality of locking arm serrated teeth defined by the locking arm, and a plurality of hub body serrated teeth defined by the hub body and sized and arranged to engage the plurality of locking arm serrated teeth to retain the tension member when the locking arm and hub body are in the releasably locked position.

6. The catheter hub according to claim 5, wherein the locking arm includes a joint positioned between the distal locking arm portion and the proximal locking arm portion such that either the distal locking arm portion or the proximal locking arm portion can rotate about the joint.

7. A catheter hub for use with a catheter and a tension member for tensioning a distal end region of the catheter, the catheter hub comprising:
a hub body defining a fluid passageway in communication with a first aperture, the hub body adapted for attachment to the catheter, the fluid passageway and the catheter aligned for fluid flow therethrough, the first aperture extending from and communicating with the fluid passageway to an exterior surface of the hub body a sealing element configured to receive the tension member therethrough, the sealing element sized for and positioned in the first aperture;

a locking arm attached to the hub body having a proximal portion and a distal portion, the distal portion positioned to cover the first aperture; and a hole defined in the distal portion of the locking arm and sized and positioned to receive the tension member therethrough;

wherein the hub body has a first side face defining a first recess and a second side face defining a second recess;

wherein the proximal portion of the locking arm has an interior surface defining a first nub receivable in the first recess and a second nub receivable in the second recess; and wherein the hub body and the locking arm are convertible between a releasably locked position in which the first nub and the second nub are received in the first recess and the second recess, respectively, and an unlocked position in which the first nub and the second nub are removed from the first recess and the second recess, respectively.

8. The catheter hub according to claim 7, wherein the hub body also defines a second aperture that intersects the first aperture, the second aperture extending from and communicating with the first aperture and the exterior surface, wherein the sealing element is sized for and positioned in both of the first aperture and the second aperture, and wherein the sealing element is configured to move in the second aperture to seal both of the first aperture and the second aperture.

9. The catheter hub according to claim 8, wherein the second aperture intersects the first aperture at an acute angle.

10. The catheter hub according to claim 8, further comprising:

a locking device attached to the hub body, the locking device configured to engage the sealing element and move the sealing element in the second aperture.

11. The catheter hub according to claim 10, the locking device having a nub configured to engage the sealing element.

12. The catheter hub according to claim 10, wherein the sealing element is compressed by the locking device.

13. A catheter hub for use with a catheter and a tension member for tensioning a distal end region of the catheter, the catheter hub comprising:

a hub body defining an inner fluid passageway in communication with a first aperture, the hub body adapted for attachment to the catheter, the inner fluid passageway and the catheter aligned for fluid flow therethrough, the first aperture extending from and communicating with the inner fluid passageway to an exterior surface of the hub body;

a sealing element configured to receive the tension member, the sealing element sized for and positioned in the first aperture, wherein the sealing element and the first aperture form a fluid-tight seal between the sealing element and the first aperture, wherein the fluid-tight seal has a first seal face and a second seal face defined respectively by first and second surfaces of the sealing element, wherein the first seal face is fluidly exposed to the exterior surface of the hub body, wherein the second seal face is fluidly exposed to the inner fluid passageway, wherein the second seal face spans laterally between longitudinally-extending wall portions extending along a direction of a longitudinal axis of the first aperture, wherein the second seal face has an outer perimeter defined at intersections between the sealing element and the longitudinally-extending wall portions, and wherein an entirety of the second seal face is fluidly exposed to the inner fluid passageway;

a locking arm attached to the hub body having a proximal portion and a distal portion, the distal portion positioned to cover the first aperture; and a hole defined in the distal portion of the locking arm and sized and positioned to receive the tension member therethrough;

wherein the hub body has a first side face defining a first recess and a second side face defining a second recess;

wherein the proximal portion of the locking arm has an interior surface defining a first nub receivable in the first recess and a second nub receivable in the second recess; and wherein the hub body and the locking arm are convertible between a releasably locked position in which the first nub and the second nub are received in the first recess and the second recess, respectively, and an unlocked position in which the first nub and the second nub are removed from the first recess and the second recess, respectively.

14. The catheter hub of claim 13, wherein the first face of the fluid tight seal is generally flush with the exterior surface of the hub body.

15. The catheter hub of claim 14, wherein the sealing element is in a compressed condition.

16. The catheter hub of claim 13, wherein the sealing element is in a compressed condition.

17. The catheter hub of claim 13, wherein the hub body defines a second aperture that intersects the first aperture and that extends from and communicates with the first aperture and the exterior surface, and wherein the sealing element is sized for and positioned in both of the first aperture and the second aperture.

* * * * *